United States Patent [19]

Besanceney

[11] Patent Number: 4,709,582

[45] Date of Patent: Dec. 1, 1987

[54] INSPECTION DEVICE FOR ROTOR BINDING DEFECTS IN ELECTRICAL MACHINES

[75] Inventor: Michel Besanceney, Plancher-Bas Centre, France

[73] Assignee: Alsthom, Paris, France

[21] Appl. No.: 836,885

[22] Filed: Mar. 6, 1986

[30] Foreign Application Priority Data

Mar. 6, 1985 [FR] France .................................. 85 03302

[51] Int. Cl.⁴ .............................................. G01N 29/04
[52] U.S. Cl. ......................................... 73/622; 73/611
[58] Field of Search ................. 73/622, 637, 641, 628, 73/611

[56] References Cited

U.S. PATENT DOCUMENTS

| | | | |
|---|---|---|---|
| 3,599,478 | 8/1971 | Weinbaum | 73/611 |
| 4,351,190 | 9/1982 | Rehme et al. | 73/622 |
| 4,375,165 | 3/1983 | de Sterke | 73/622 |
| 4,502,331 | 3/1985 | Singh et al. | 73/627 |

FOREIGN PATENT DOCUMENTS 1559469 1/1980 United Kingdom .
2053474A 2/1981 United Kingdom .

OTHER PUBLICATIONS

Patent Abstracts of Japan, vol. 8, No. 237, (P-310) Oct. 30, 1984.

Primary Examiner—Stewart J. Levy
Assistant Examiner—Louis M. Arana
Attorney, Agent, or Firm—Sughrue, Mion, Zinn, Macpeak, and Seas

[57] ABSTRACT

In a rotor binding inspection device comprising a self-powered carriage movable about the rotor shaft and a probe-carrying arm carried by said carriage and operable to move longitudinally parallel to the axis of the rotor between the stator and the rotor binding, said arm carrying at its extremity two detector units each comprising a right angle, longitudinal wave probe and an oblique angled, transverse wave probe, additional means are provided for recording the right angle probe echoes, for recording the angled probe echoes and for defining for the angled probes, based upon the indications from the right angle probes, a variable detection threshold.

7 Claims, 5 Drawing Figures

INSPECTION DEVICE FOR ROTOR BINDING DEFECTS IN ELECTRICAL MACHINES

This invention concerns a device for inspecting electrical machine rotor bindings for defects, said device comprising a self-powered carriage movable about the rotor shaft and a probe-carrying arm carried by said carriage and operable to move longitudinally parallel to the axis of the rotor between the stator and the rotor binding, said arm carrying at its extremity two detector units each comprising a right angle, longitudinal wave probe and an oblique angled, transverse wave probe, each of the latter being symmetrically inclined with respect to the radii of the rotor and acting simultaneously as transmitter and receiver.

Inspection of electrical machine rotor bindings for defects, and in particular of alternator rotor binding bands, at present generally involves extracting the rotor from its stator to inspect it, most often visually.

Devices are known in the prior art for inspecting metallurgical parts by reflection of ultrasonic waves and recording of the amplitude of the received signal. It would thus be possible to envisage inspecting a rotor without extracting it from its stator, using a movable carriage supporting a probe arm as specified above. However, problems arise with this concept, primarily because echoes from binding defects can be stronger or weaker than the form echoes from the rotor teeth and because defects with identical dimensions produce echoes of different amplitudes according to whether the defect is located in a binding zone (on a rotor tooth) or not (between teeth or area outside the binding area). Ultrasonic flaw detection without discrimination between signals would require complex data reduction and analysis involving an identification of form echoes and lookup of abnormal echoes likely to indicate defects—a complicated, time-consuming and error-prone process requiring excessive lengths of recording medium.

The present invention is accordingly directed to providing a defect inspection device for electrical machine rotor bindings, not requiring removal of the rotor, which enables easy discrimination between rotor form and defect echoes, affords sufficient detection sensitivity regardless of the location of a flaw and enables quick and accurate determination of defects on reading the recordings whilst minimizing the risks of error.

The device according to the invention consists of:
means for recording the echoes from the right angle probes defining the strength of acoustic coupling, the thickness of the binding band, the location of the inspection point—whether in a bound or unbound zone—and its angular and linear positions,
  means for recording the echoes from the angled probes within a time interval centered on the time of coverage of the inspected zone,
  and control means defining for the oblique angled probes, on the basis of the indications from the right angle probes, a detection threshold varying in height according to whether the inspected point is located in a bound zone or an unbound zone.

It moreover preferably includes at least one of the following features:
  The angled probe echo recording means are each provided with an amplifier having two different gains.
  The movements of the self-powered carriage and the probe carrying arm are controlled by a computer programmed with instructions regarding the angular and longitudinal recording interval units, the choice of the recording time span for the probes according to the thickness of the binding band and the reading of the angular and longitudinal coordinates.
  The computer is provided with an instruction for determining the average of the amplitudes of the signals received by each of the oblique angled probes and recording said average value alone.

The above features as well as the operation of a device according to the invention will now be described in detail with reference to the appended drawings relating to a preferred embodiment for the inspection of the rotor bindings of a high powered turbine-type AC generator.

FIG. 1 schematically illustrates a two-detector-unit assembly and shows the ultrasonic beam paths.

Figure 1:
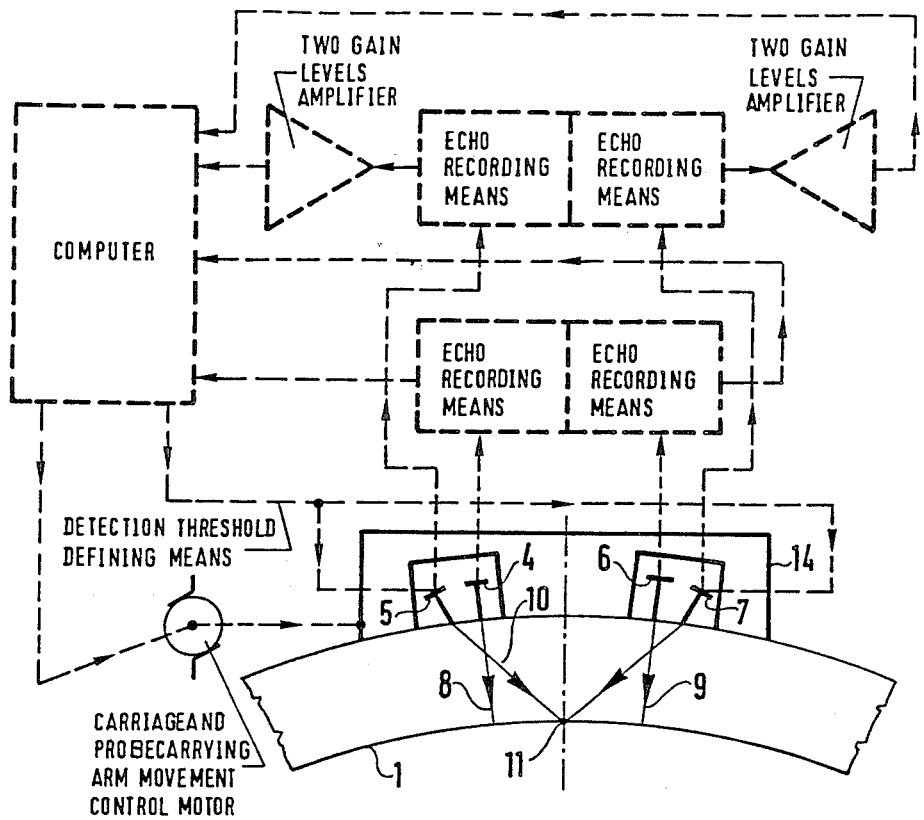

In FIG. 1, the two detector units 2, 3 can be seen facing the rotor binding band or retaining ring 1. Said two units are mounted on a probe-carrying arm attached to an intermediate plate on a self-powered carriage, none of which latter items are shown. As can be seen, the unit 2 includes a right angle probe 4, which emits longitudinal waves, and an oblique or "angled" probe 5, which emits transverse waves. Likewise, the unit 3 includes a right angle probe 6 and angled probe 7. The right angle probes emit longitudinal wave ultrasonic beams 8, 9 which reflect back from the inside wall of the binding band. The angled probes emit transverse wave beams which follow path 10 through the rotor band. The beams emitted by probes 5 and 7 converge on the inside surface of the binding band 1 at point 11. In keeping with usual ultrasonics practice, liquid is injected for coupling purposes at the interface between the band and the sensors or probes and is later recovered by suction.

Figure 2:
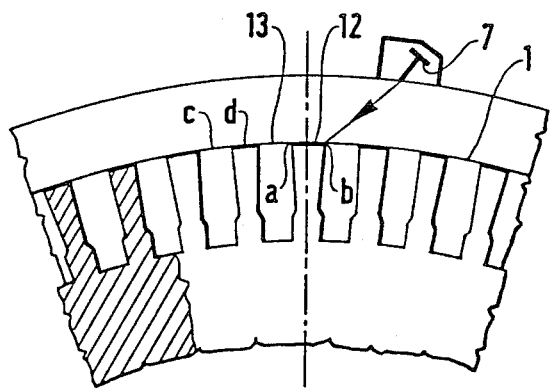
FIG. 2 shows a small part of the rotor with the various possible points of defect localization.

FIG. 2 shows the basic structure of the periphery of the rotor, which comprises teeth 12 and interteeth intervals 13.

Figure 4:
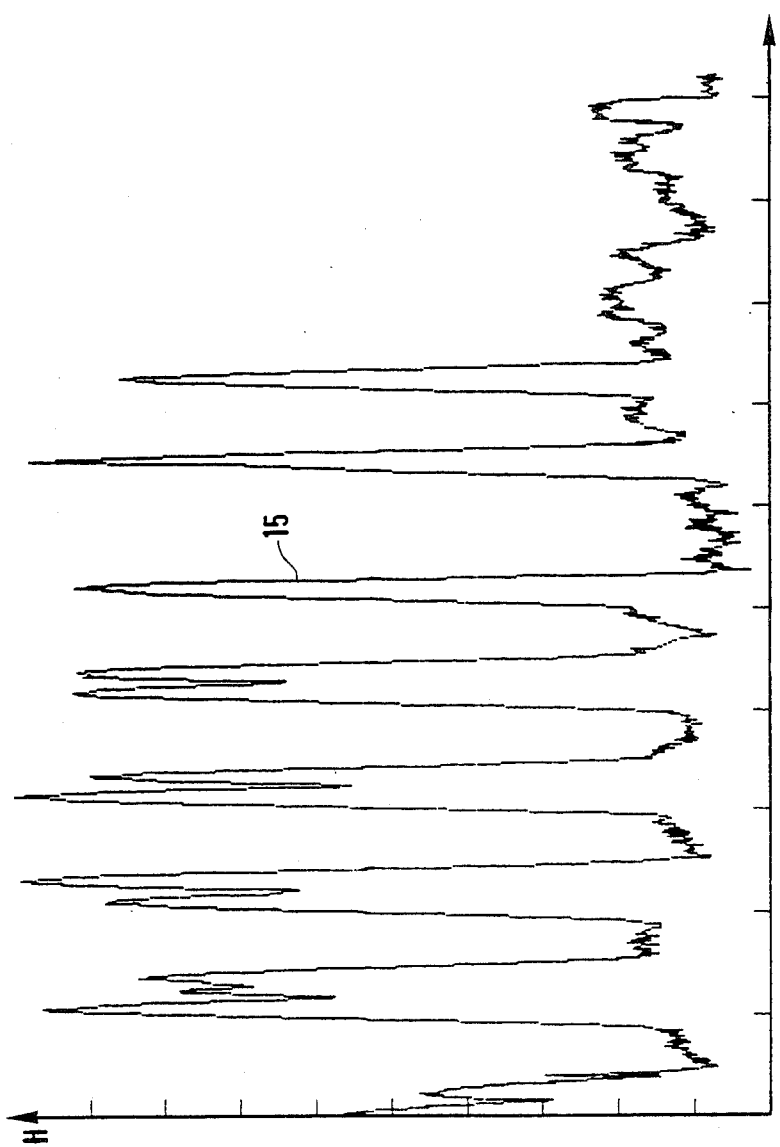
FIG. 4 is an element of an echograph of the signals from an angled probe.

As the probe-carrying arm rotates around the band 1, the beam of ultrasonic waves from an angled probe is successively reflected by the front edge of a rotor tooth (point a), then by the top of a tooth (such as point d), then by the back edge (point b) and between two teeth (point c) and so on. Each of these successive reflections produces an echo which appears on the echograph in the form of a peak such as peak 15 in FIG. 4. Depending on the size and position of any defect found, which may occur anywhere among the points a, b, c or d, the echo produced by said defect will be either stronger or weaker than the echoes from the rotor teeth (shape echoes) or even be confounded with one of the latter echoes. Moreover, two defects of equal size will produce echoes with different amplitudes according as they are located at a point such as c (between teeth) or d (on a tooth). In the first case, all of the ultrasound energy remains in the binding band and will thus be reflected by the defect. In the second case, a large part of the ultrasound energy passes through the bound interface and gets lost in the tooth; the defect will reflect only a fraction of the incident energy.

Figure 3:
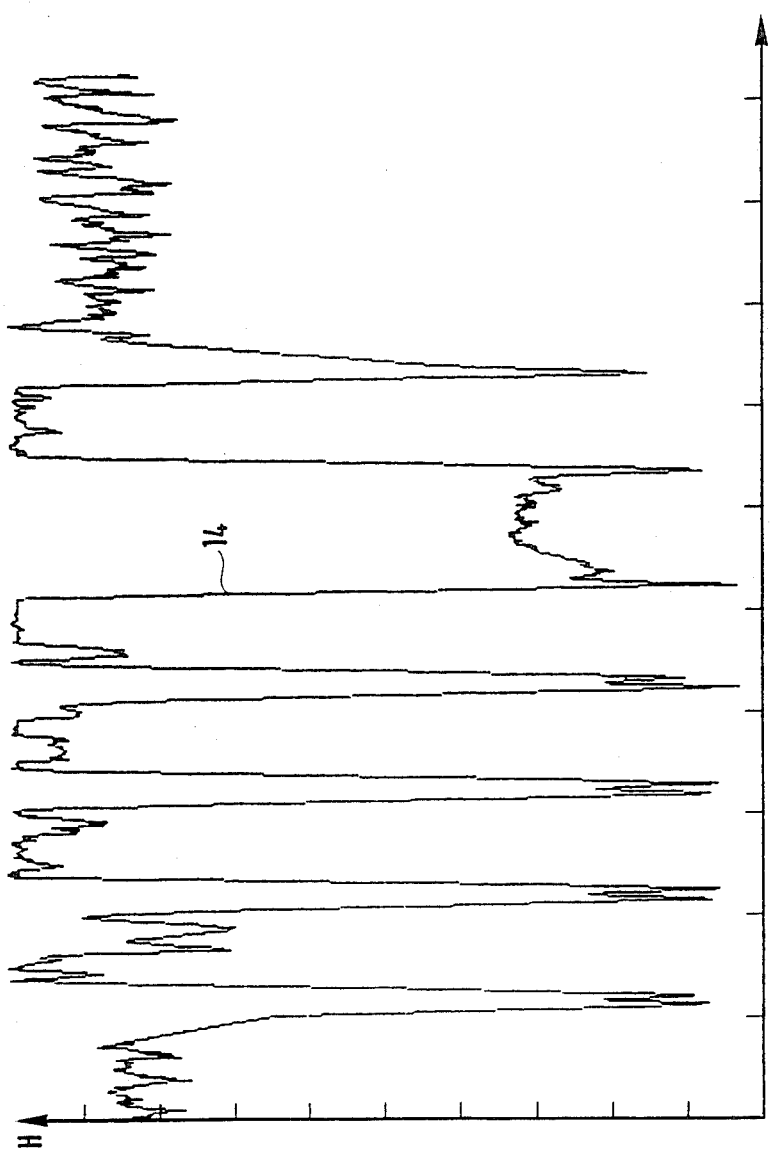
FIG. 3 is an element of an echograph of the signals from a right angle probe.

The signals are processed as follows:

The signals from each of the longitudinal wave, right angle probes, corresponding to the amplitude of the echo and the travel time of the ultrasonic beam through the binding band, are collected (FIG. 3). These signals yield an echograph plotted with abscissa coordinates L and ordinates H, and displaying a number of peaks 14. The signals, of which there are four altogether, define:

the strength of acoustic coupling,
the thickness of the binding band,
and the location of the probe, ie. whether in a binding (shrunk) zone or unbound (nonshrunk) zone.

The signals from each of the transverse wave, oblique angled probes corresponding to the amplitude of the echo and the travel time of the ultrasonic beam through the binding band are also collected. These signals are acquired twice, using two different gains fo the ultrasonic device so as to artificially augment the dynamic range of the device and more easily screen out background noise.

The echo amplitude signals are collected within a "gate" centered on the travel time correspoinding to the inspection zone. The width of this gate is determined as a function of the desired resolution and the type of information being sought.

To start the recording, a longitudinal wave probe is placed on an unbound zone of the rotor and the computer reads the travel time OL.

The observation gate is then positioned manually and the computer reads the travel time OT of the transverse wave probe.

The ratio of these two travel times OL:OT, is a homothetic ratio which enables the gate to be correctly positioned according to changes in band thickness.

The signals from the four, geometrically offset probes are realigned with the axis of the probe-carrying arm.

The ultrasonic energy reflected by a flaw and therefore the amplitude of the echo it provides, differing according to the probe's aiming at a bound zone (on a tooth) or not (between teeth or outside of the binding area), is such that the amplitude data supplied by the longitudinal wave probes serves to define a threshold that varies according to whether the inspected zone is bound or not, so as to maintain a substantially constant detection sensitivity with respect to the flaws.

Figure 5:
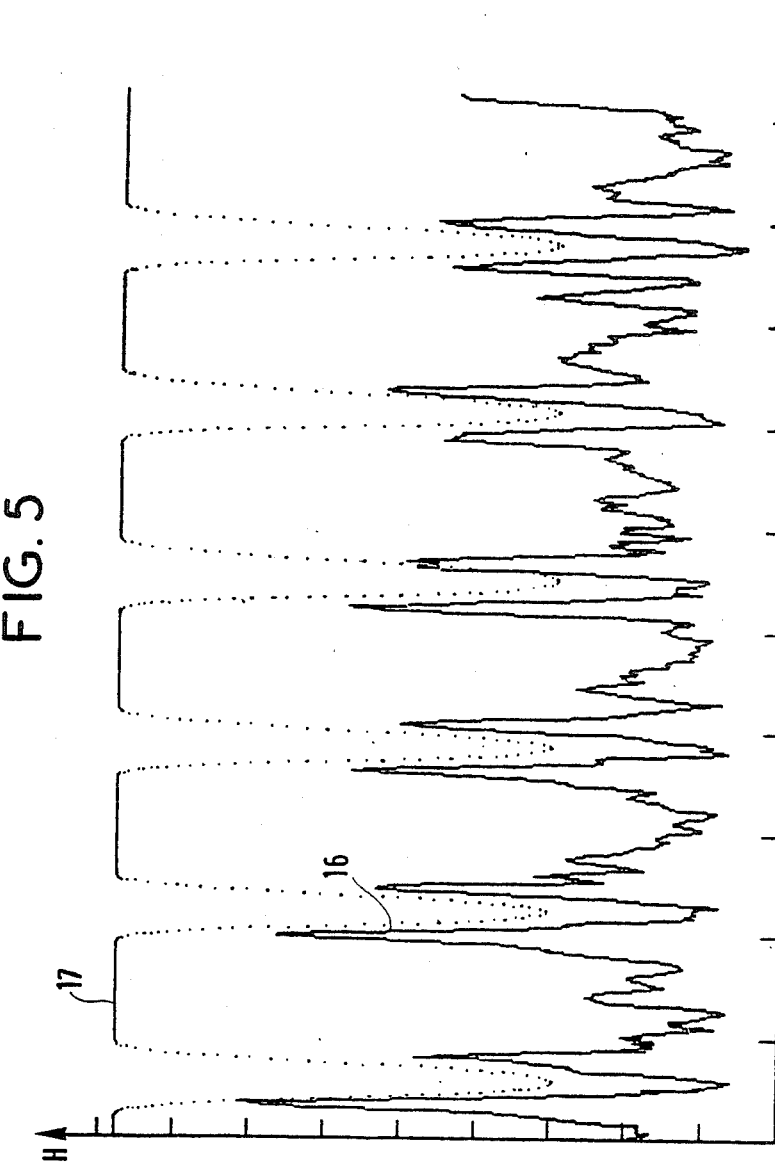
FIG. 5 is an element of an ecograph of the averaged signals from two angled probes.

The L-abscissa and H-ordinate echograph of the transverse wave probes (FIG. 4) contains form-echoes (peaks 15) as well as any fault echoes as may occur. After averaging these signals, an echograph with peaks 16 is obtained, as shown in FIG. 5. Any overshoots of the variable threshold 17 indicate an anomaly and thus the liklihood of a flaw.

Data acquisition can be carried out, for example, every 20 milliseconds, which corresponds to a circumferential length of 0.5 mm at an inspection speed of 25 mm/s.

An acquisition time lasts 600 microseconds, so leaving a little more than 19 milliseconds for real time processing of the data.

The data can be saved after processing in digital form on magnetic tape, in which case only one gain value is stored for the signals from the transverse wave probes.

The results are recorded in graphic form, either on a display screen or on paper after automatic retranscription. Each graphic display can correspond, for example, to 250 mm of circumferential length out of the total length of the binding band.

The computer checks the motions of the probe-carrying arm and the carriage and transmits motion instructions to the control box. Its programmed functions include the following:

start/stop control, defining the sweep angle (in circumferential length, + and −along the X-axis),
defining the longitudinal increment (+ and − along Y-axis),
reading of X and Y values,
stopping as result of acoustic coupling failure,
and returning the mechanical assembly to an X-Y coordinate point.

What is claimed is:

1. Device for inspecting electrical machine rotor bindings for defects, comprising a self-powered carriage movable about the rotor shaft and a probe-carrying arm carried by said carriage and operable to move longitudinally parallel to the axis of the rotor between the stator and the rotor binding, said arm carrying at its extremity two detector units each comprising a right angle, longitudinal wave probe and an oblique angled, transverse wave probe, each of the latter being symmetrically inclined with respect to the radii of the rotor and acting both as transmitter and receiver, wherein are additionally provided:

means for recording the echoes from the right angle probes defining the strength of the acoustic coupling, the thickness of the binding band and the location—in or outside the binding zone—of the inspection point, means for recording the echoes from the oblique-angled probes within a time interval centered on the travel time corresponding to the inspected zone, and means of control defining for the oblique-angled probes, on the basis of the indications from the right angle probes, a detection threshold varying in height according to whether the inspection point is located in a bound zone or an unbound zone.

2. Inspection device according to claim 1, wherein said means for recording the echoes associated with the oblique-angled probes are each provided with an amplifier having two different gains.

3. Inspection device according to claim 2, wherein the movements of the self-powered carriage and the probe-carrying arm are controlled by a computer supplied with instructions regarding the angular and longitudinal recording interval units, the choice of the recording time span for the probes according to th thickness of the binding band and the reading of the angular and longitudinal coordinates.

4. Device according to claim 3, wherein said computer is programmed to determine the average of the amplitudes of the signals received by each of the oblique angled probes and to record said average value alone.

5. A method for inspecting electrical machine rotor bindings for defects of an electrical machine having a rotor, a stator, a rotor shaft mounting said rotor for rotation rotation about its axis, a probe-carrying arm carried by said carriage and operable to move longitudinally parallel to the axis of the rotor between the stator and rotor binding, said arm carrying at its extremity two detector units, each comprising a right angle, longitudinal wave probe and oblique angle, transverse wave probe, each of the latter being symmetrically inclined with respect to the radius of the rotor and acting both as transmitter and receiver, said method comprising moving said self-powered carriage about the rotor shaft and moving said probe-carrying arm carried by said carriage longitudinally parallel to the axis of the rotor between the stator and the rotor binding; the improvement comprising the steps of:
- recording the echoes from the right angle probes defining the strength of the acoustic coupling, the thickness of the binding band and the location—in or outside the binding zone—of the inspection point,
- recording the echoes from the oblique angled probes within a time interval centered on the travel time corresponding to the inspected zone,
- and defining for the oblique-angled probes, on the basis of the indications from the right angle probes, a detection threshold which varies in height according to whether the inspection point is located in a bound zone or an unbound zone.

6. The method according to claim 5, further comprising the step of contorlling the movements of the self-powered carriage and the probe-carrying arm by a computer supplied with instructions regarding the angular and longitudinal recording interval units, the choice of the recording time span for the probes according to the thickness of the binding band and the reading of the angular and longitudinal coordinates.

7. The method according to claim 6, futher comprising the step of determining the average of the amplitudes of the signals received by each of the oblique angled probes in recording said average value alone.

* * * * *